US010209196B2

(12) United States Patent
Day (10) Patent No.: US 10,209,196 B2
(45) Date of Patent: Feb. 19, 2019

(54) LIBS ANALYSIS SYSTEM AND METHOD FOR LIQUIDS (71) Applicant: SciAps, Inc., Woburn, MA (US)

(72) Inventor: David R. Day, Boxford, MA (US)

(73) Assignee: SciAps, Inc., Woburn, MA (US)

( * ) Notice: Subject to any disclaimer, the term of this patent is extended or adjusted under 35 U.S.C. 154(b) by 0 days.

(21) Appl. No.: 15/697,868

(22) Filed: Sep. 7, 2017

(65) Prior Publication Data

US 2018/0003640 A1 Jan. 4, 2018

Related U.S. Application Data (63) Continuation-in-part of application No. 14/874,726, filed on Oct. 5, 2015, now Pat. No. 9,552,100.

(51) Int. Cl.
*G01J 3/02* (2006.01)
*G01N 21/71* (2006.01)
*G01N 33/14* (2006.01)
*G01N 33/28* (2006.01)
*G01N 33/18* (2006.01)
*G01J 3/28* (2006.01)
(Continued)

(52) U.S. Cl.
CPC .......... *G01N 21/718* (2013.01); *G01J 3/0272* (2013.01); *G01J 3/0286* (2013.01); *G01J 3/0291* (2013.01); *G01J 3/2823* (2013.01); *G01J 3/30* (2013.01); *G01J 3/443* (2013.01); *G01N 33/146* (2013.01); *G01N 33/18* (2013.01); *G01N 33/28* (2013.01); *G01N 2201/0221* (2013.01); *G01N 2201/06113* (2013.01); *G01N 2201/13* (2013.01)

(58) Field of Classification Search
CPC ........ G01N 21/67; G01N 21/01; G01N 15/02; G01N 15/14; G01N 33/28; G01N 33/18; G01N 21/71; G01J 3/02
See application file for complete search history.

(56) References Cited

U.S. PATENT DOCUMENTS 3,760,144 A  9/1973 Herzberger
4,358,659 A  11/1982 Spohnheimer
4,770,486 A  9/1988 Wang
(Continued)

FOREIGN PATENT DOCUMENTS

WO  WO2012040769 A1  4/2012
WO  WO2012135961 A1  10/2012
(Continued)

OTHER PUBLICATIONS

Written Opinion of the International Searching Authority for PCT Application No. PCT/US2014/11961 dated May 8, 2014 (six (6) pages).
(Continued)

*Primary Examiner* — Abdullahi Nur
(74) *Attorney, Agent, or Firm* — Iandiorio Teska & Coleman, LLP (57) ABSTRACT A LIBS analysis system and method for liquids wherein a handheld LIBS analyzer has a nose section through which a laser beam passes. A sample holder positioner is attached to the nose section of the hand held LIBS analyzer. A sample holder is receivable in the sample holder positioner and includes a container for a liquid and an opening for filling the container with the liquid.

42 Claims, 6 Drawing Sheets (51) Int. Cl.
*G01J 3/30* (2006.01)
*G01J 3/443* (2006.01)

(56) References Cited

U.S. PATENT DOCUMENTS

| | | | |
|---|---|---|---|
| 5,473,162 A | 12/1995 | Busch et al. | |
| 5,520,679 A | 5/1996 | Lin | |
| 6,006,140 A | 12/1999 | Carter | |
| 6,077,386 A | 6/2000 | Smith, Jr. et al. | |
| 6,355,908 B1 | 3/2002 | Tatah et al. | |
| 6,568,418 B1 | 5/2003 | Hope et al. | |
| 6,801,595 B2 | 10/2004 | Grodzins et al. | |
| 6,936,229 B1 | 8/2005 | Boryta et al. | |
| 7,233,643 B2 | 6/2007 | Spila et al. | |
| 7,394,537 B1 | 7/2008 | Lindfors et al. | |
| 7,426,019 B2 | 9/2008 | Eklin | |
| 7,821,634 B2 | 10/2010 | Dillon et al. | |
| 8,184,287 B2 | 5/2012 | Hamilton et al. | |
| 8,199,321 B2 | 6/2012 | Yoo et al. | |
| 8,436,991 B2 | 5/2013 | Senac | |
| 8,655,807 B2 | 2/2014 | Multari et al. | |
| 8,687,189 B2 | 4/2014 | Agrawal et al. | |
| 9,360,367 B2 | 6/2016 | Day et al. | |
| 9,366,634 B2 | 6/2016 | Wang et al. | |
| 9,506,869 B2 | 11/2016 | Quant et al. | |
| 9,651,424 B2 | 5/2017 | Day et al. | |
| 2001/0015801 A1 | 8/2001 | Hirose et al. | |
| 2002/0009814 A1 | 1/2002 | Usui et al. | |
| 2003/0010907 A1 | 1/2003 | Hayek et al. | |
| 2003/0174325 A1 | 9/2003 | Zhang et al. | |
| 2003/0234928 A1 | 12/2003 | Lucas et al. | |
| 2004/0183010 A1 | 9/2004 | Reilly et al. | |
| 2005/0032459 A1 | 2/2005 | Surana et al. | |
| 2005/0056628 A1 | 3/2005 | Hu | |
| 2005/0068524 A1 | 3/2005 | Wu et al. | |
| 2005/0142260 A1 | 6/2005 | Chen et al. | |
| 2005/0236563 A1 | 10/2005 | Busch et al. | |
| 2005/0248758 A1 | 11/2005 | Carron et al. | |
| 2006/0100676 A1 | 5/2006 | Walmsley | |
| 2006/0262302 A1 | 11/2006 | Eklin | |
| 2007/0187632 A1 | 8/2007 | Igarashi | |
| 2007/0195311 A1 | 8/2007 | Morgan | |
| 2007/0202613 A1 | 8/2007 | Usui | |
| 2007/0265783 A1 | 11/2007 | Mound | |
| 2008/0151241 A1 | 6/2008 | Lindfors et al. | |
| 2008/0165344 A1 | 7/2008 | Treado et al. | |
| 2008/0205755 A1 | 8/2008 | Jackson | |
| 2008/0259330 A1 | 10/2008 | Dillon et al. | |
| 2009/0007933 A1 | 1/2009 | Thomas et al. | |
| 2009/0025761 A1 | 1/2009 | Matsumoto | |
| 2009/0057422 A1 | 3/2009 | Dugas et al. | |
| 2009/0103082 A1 | 4/2009 | Black et al. | |
| 2010/0197116 A1 | 8/2010 | Shah et al. | |
| 2011/0100967 A1 | 5/2011 | Yoo et al. | |
| 2011/0246145 A1 | 10/2011 | Multari et al. | |
| 2011/0315661 A1 | 12/2011 | Morisawa | |
| 2012/0029836 A1 | 2/2012 | Hermann | |
| 2012/0044488 A1 | 2/2012 | Senac | |
| 2012/0085366 A1 | 4/2012 | Hirota | |
| 2012/0162642 A1 | 6/2012 | Watson et al. | |
| 2012/0206722 A1 | 8/2012 | Grigoropoulos et al. | |
| 2012/0236303 A1 | 9/2012 | Marple et al. | |
| 2012/0268743 A1 | 10/2012 | Wang et al. | |
| 2012/0314214 A1 | 12/2012 | Aleander et al. | |
| 2013/0016349 A1 | 1/2013 | Effenberger, Jr. et al. | |
| 2013/0271761 A1 | 10/2013 | Rutberg et al. | |
| 2013/0342902 A1 | 12/2013 | Krueger | |
| 2014/0022531 A1 | 1/2014 | Sackett | |
| 2014/0022532 A1 | 1/2014 | Sackett | |
| 2014/0125965 A1 | 5/2014 | Nagli | |
| 2014/0202490 A1 | 7/2014 | Day | |
| 2014/0204375 A1 | 7/2014 | Day | |
| 2014/0204376 A1 | 7/2014 | Day | |
| 2014/0204377 A1 | 7/2014 | Day et al. | |
| 2014/0204378 A1 | 7/2014 | Day | |
| 2015/0103334 A1* | 4/2015 | Quant | G01N 21/718 356/51 |
| 2016/0084709 A1 | 3/2016 | Day et al. | |
| 2016/0187201 A1 | 6/2016 | Wang et al. | |
| 2016/0252398 A1 | 9/2016 | Day et al. | |

FOREIGN PATENT DOCUMENTS

| | | |
|---|---|---|
| WO | WO2013083950 A1 | 6/2013 |
| WO | WO2015057784 A1 | 4/2015 |

OTHER PUBLICATIONS

Written Opinion of the International Searching Authority for PCT Application No. PCT/US2014/11863 dated May 13, 2014 (nine (9) pages).
Written Opinion of the International Searching Authority for PCT Application No. PCT/US2014/016188 dated Feb. 2, 2015 (eight (8) pages).
Written Opinion of the International Searching Authority for PCT Application No. PCT/US2014/12060 dated Jan. 27, 2015 (five (5) pages).
Thorlabs, "Off-Axis Parabolic Mirrors With Holes Parallel to Collimated Beam", http://www.thorlabs.us/newgrouppage9.cfm?objectgroup_id=8172, Aug. 13, 2015, (two (2) pages).
Thorlabs, "Off-Axis Parabolic Mirrors With Holes Parallel to Focused Beam", http://www.thorlabs.us/newgrouppage9.cfm?objectgroup id=7197, Aug. 12, 2015, Three (3) pages).
Ocean Optics, Laser-Induced Breakdown Spectroscopy, The LIBS2500plus LIBS Systems, http://www.oceanoptics.com/products/libs.asp, (four (4) pages).
Applied Photonics, LIBSCAN 25, brochure, (two (2) pages).
Oxford Instruments, Laser Induced Breakdown Spectroscopy (LIBS), http://www.oxford-instruments.com/products/spectrometers/laser-induced-bre . . . , (two (2) pages).
RMG Technology Introduces Hand-Held Laser Analyzer, Recycling Today, http://www.recyclingtoday.com/Article.aspx?article_id=141665, (two (2) pages).
Applied Spectra, Inc., Model RT100-EC, http://www.appliedspectra.com/products/rt100-ec.html, (four (4) pages).

* cited by examiner

LIBS ANALYSIS SYSTEM AND METHOD FOR LIQUIDS

RELATED APPLICATIONS

This application is a continuation-in-part of U.S. patent application Ser. No. 14/874,726 filed Oct. 5, 2015 and claims the benefit of and priority thereto under 35 U.S.C. §§119, 120, 363, 365, and 37 C.F.R. §1.55 and §1.78, which is incorporated herein by this reference.

FIELD OF THE INVENTION

The subject invention relates to laser induced breakdown spectroscopy (LIBS).

BACKGROUND OF THE INVENTION

A handheld LIBS analyzer may include a housing enclosing a laser source, one or more spectrometers, and various optical and electronic components. The laser beam passes out of the housing via the nose section thereof. See U.S. Pat. No. 9,360,367; U.S. pending patent application Ser. No. 14/874,726; and U.S. Pat. Nos. 7,426,019; 8,436,991; 7,394,537; and 9,506,869 all incorporated herein by this reference.

In some instances, it would be desirable to use a handheld LIBS analyzer to analyze liquids. For example, in the field of lithium brines, currently a sample is taken from the brine location and sent to a laboratory to analyze the present lithium concentration. This process, however, can take several days or even weeks. The lithium content may also be an important variable in recovery methods. See U.S. Pat. No. 6,936,229 incorporated herein by this reference. Oil analysis, for example, is another area where a handheld LIBS analyzer could be used. See U.S. Pat. No. 9,366,634 incorporated herein by this reference.

As noted in U.S. Pat. No. 8,687,189, incorporated herein by this reference, analysis of liquids is difficult using a handheld LIBS device since the laser pulse dumps a large amount of energy which sends a shock wave and splatters the liquid which interferes with the physical observation of the emission due to liquid or dried residue on the device optics and which can also cross contaminate the next sample.

SUMMARY OF THE INVENTION

Still needed, then, is a LIBS analysis system for liquids which is easy to use and low in cost.

Liquid measurements are possible using bench top LIBS systems where the focal lengths are larger and optics are quite a distance from the plasma (several 10's of mm). With handheld LIBS, the focusing and protection optics are very close to the plasma, typically within a few mm. For this reason, small splashes of the water are more likely to coat the optics and cause laser defocusing and thus plasma inhibition. One the main causes of splashing is when a plasma is formed in water with bubbles present.

In this invention we describe several preferred means of insuring bubble are not present including low shot frequency and the use of convex meniscuses to help migrate bubble away from the plasma region.

Another problem with handheld LIBS is that the spectral intensities and intensity ratios of emission lines are strongly dependent on how far the water surface is from the focusing lens. In aspects of this invention, we describe the components and construction that allow for very reproducible water surface location relative to the focusing lens.

Featured is a LIBS analysis system for liquids comprising a handheld LIBS analyzer with a nose section through which a laser beam passes. A sample holder positioner is attached to the nose section of the hand held LIBS analyzer. A sample holder is receivable in the sample holder positioner and includes a container for a liquid and a top opening for filling the container with the liquid.

In one version, the nose section includes an end plate with an orifice therethrough for the laser beam and the positioner is affixed to the end plate. The end plate may be adapted for liquid samples and includes an enlarged orifice therethrough. The positioner may include a socket about the end plate orifice and receiving the sample holder therein.

Preferably, the sample holder top opening is non-circular (e.g., oval shaped) to dampen shock waves produced in the liquid by the laser beam. The sample holder may further include a standoff spacing the top opening from the end plate when the sample holder is placed in the positioner. In one example, the standoff includes a rim about the top opening. The sample holder may include a top surface and then the top opening may be located in the top surface.

Preferably, the sample holder is filled with liquid forming a liquid meniscus above the opening. Also, it may be preferred that the handheld UBS analyzer is configured to direct the laser beam at a location on the liquid meniscus other than at the apex of the liquid meniscus. Also, it may be preferred that the handheld LIBS analyzer is configured to produce a pulsed laser beam at a frequency sufficient to allow any bubbles created in the liquid meniscus to migrate and/or dissipate. The frequency may be 2 Hz or less. The liquid analyzed may be a lithium brine, oil or alcoholic beverage, for example. In some examples, the handheld LIBS analyzer is configured with a purge gas delivery subsystem.

In one design, the sample holder has a longitudinal axis and the top opening is tilted along an axis at an angle to the longitudinal axis. The system may further include a calibration standard receivable in the positioner. In one example, the calibration standard includes a top surface receivable into the nose section when the calibration standard is placed in the sample holder.

Also featured is a method of analyzing liquids using a handheld LIBS analyzer. The handheld LIBS analyzer is equipped with a sample holder positioner. A liquid is loaded into a sample holder configured to be inserted into the positioner. The sample holder is placed into the positioner the handheld LIBS analyzer is operated to analyze the liquid in the sample holder.

The positioner may be affixed to an end plate of the analyzer. One method includes tilting the handheld LIBS analyzer during the analysis to encourage any bubbles formed to migrate away from the laser beam location on the sample.

Also featured is a LIBS analysis system for liquids. A sample holder positioner is attachable to the nose section of a hand held LIBS analyzer and includes a socket. A sample holder is receivable in the sample holder positioner socket and includes a container for a liquid sample and an opening for filling the container with the liquid sample. The system may further include an end plate adapted for liquid samples and including an enlarged orifice therethrough. The end plate is attachable to the analyzer and the positioner is attachable to the end plate.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 1:
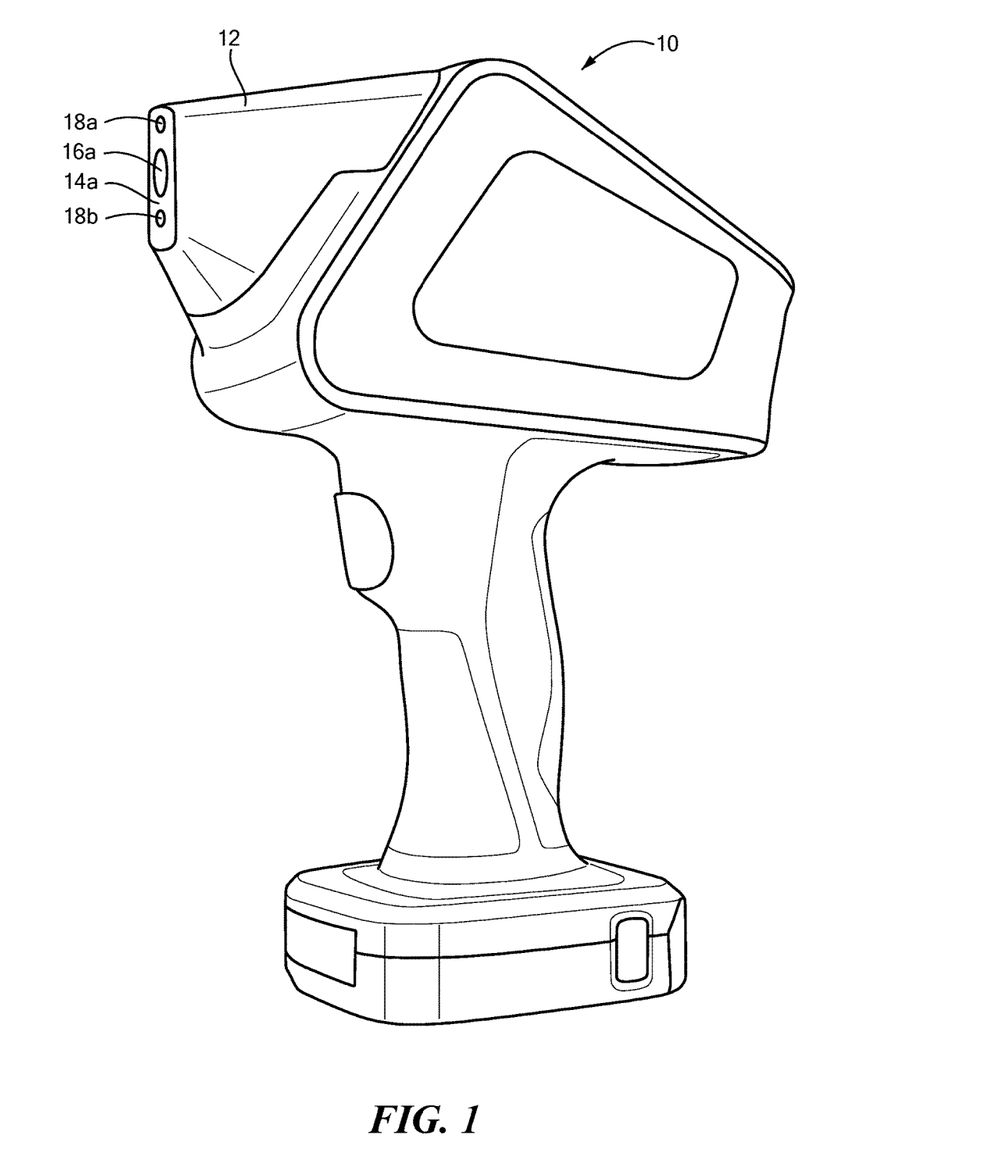
FIG. 1 is a schematic three dimensional front view showing an example of a handheld LIBS analyzer which can be used in the invention.

FIG. 1 shows an example of a handheld LIBS analyzer 10. See U.S. Pat. No. 9,360,367 and pending application Ser. No. 14/874,726 both incorporated herein by this reference.

The laser beam exits the nose section 12 which, in this particular example, includes removable end plate 14a with small opening 16a for the laser beam and fastened to the nose section 12 via fasteners 18a, 18b.

Figure 2:
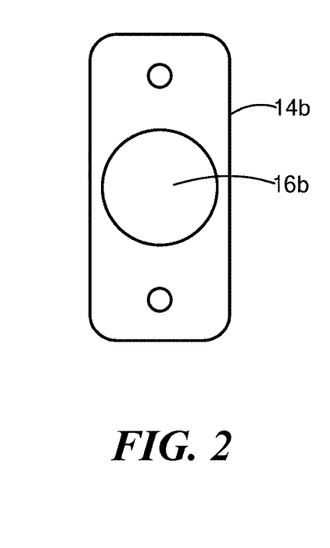
FIG. 2 is a schematic front view showing an example of an end plate for use when the analyzer of FIG. 1 is used to analyze a liquid.
Figure 3:
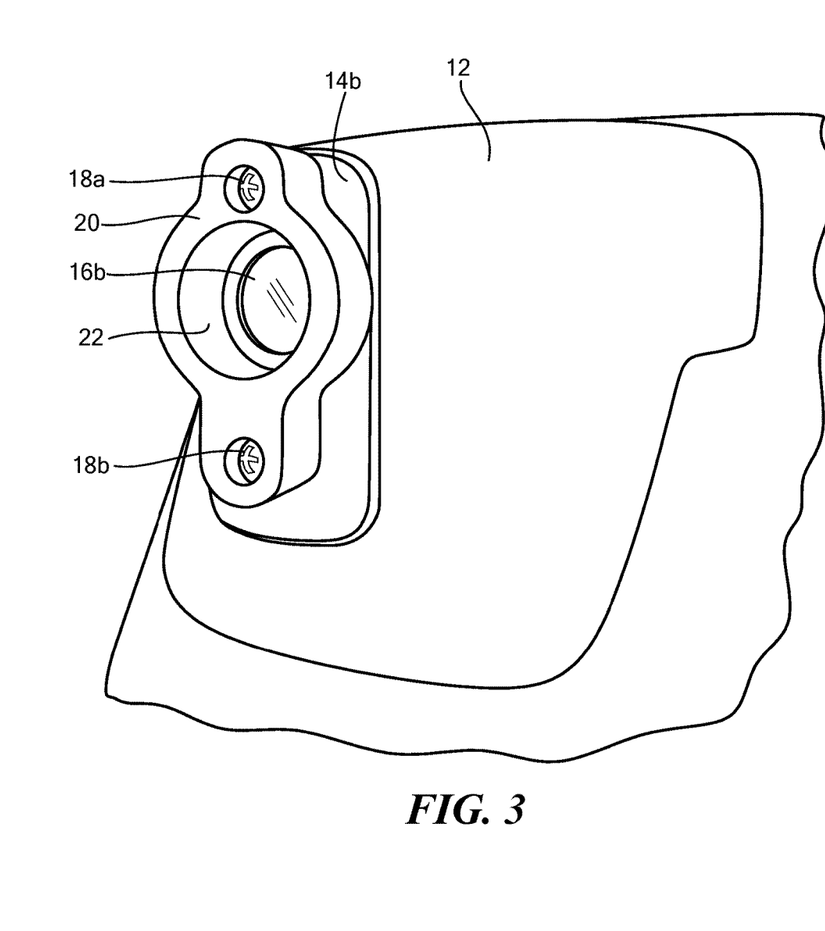
FIG. 3 is a schematic view showing the analyzer of FIG. 1 fitted with the end plate of FIG. 2 as well as a sample holder positioner.

In one preferred embodiment, when the LIBS unit is to be used to analyze a liquid sample, these fasteners are removed and end plate 14b, FIG. 2 is used instead with an enlarged opening 16b. This end plate is secured to nose section 12 of analyzer 10 as shown in FIG. 3 using fasteners 18a, 18b. Enlarged opening 16b may be about 1 cm in diameter.

In this particular embodiment, sample holder positioner 20 is also attached to the nose section of the analyzer, in this example using fasteners 18a, 18b, to a fix positioner 20 to nose plate 14b. Positioner 20 includes socket 22 about enlarged nose plate opening 16b configured to receive sample holder 30, FIG. 4 therein. Other sample holder designs are possible.

If at any time liquid splashes onto the shield inside the analyzer nose section behind opening 16b, FIG. 3 of the end plate 14b, the enlarged opening 16b of the end plate facilitates cleaning of the shield using, for example, a cotton swab.

Figure 4:
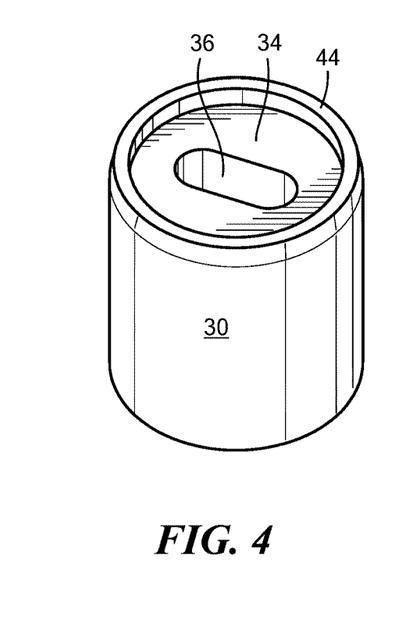
FIG. 4 is a schematic view of a sample holder in accordance with one example of the invention.
Figure 5:
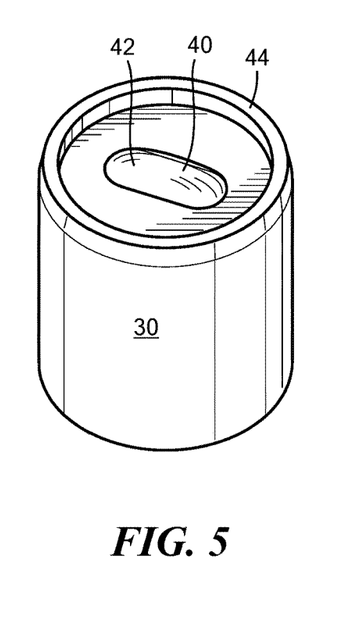
FIG. 5 is a schematic view showing the sample holder of FIG. 4 filled with liquid forming a liquid meniscus surface at the sample holder top opening.

The sample holder 30, FIG. 4, in this particular embodiment includes cylindrical container interior 32 for the liquid and top surface 34 with top opening 36 therein leading into the container for filling it with the liquid sample to be analyzed. The sample holder may take other forms but preferably is configured to be received in the sample holder positioner 20, FIG. 3 (e.g., into the socket 22 thereof). Preferably, top opening 36 of holder 30 is not circular to dampen shock waves produced in the liquid 40, FIG. 5 by the laser beam of the handheld analyzer. An oval shaped opening is shown in FIGS. 4-5. The opening, however, may take other shapes. Also, when sample holder 30 container 32 is filled as shown in FIG. 5, the liquid 40 forms a convex meniscus as shown. The handheld LIBS analyzer 10, FIG. 1 can be configured to direct the laser beam at a location such as location 42 on the liquid meniscus other than the apex thereof. In this way, a bubble formed by the laser beam at location 42 will eventually migrate up to the apex of the liquid meniscus and not interfere with the next laser pulse at location 42. As discussed in U.S. Pat. No. 9,360,367 and pending application Ser. No. 14/874,726, the handheld laser preferably includes an optics stage whereby the focusing lens can be moved in order to direct a laser beam to location 42. In some embodiments, the sample holder is positioned in the positioner such that the long axis of the oval extends left to right across the nose section of the analyzer in order to more easily move the laser beam to a position such as position 42 shown in FIG. 5. In some embodiments, there may be a keying arrangement between the positioner and the sample holder so that the sample holder can only be inserted into the positioner in one fashion.

Also, if the laser is pulsed at a frequency which allows the bubbles to migrate away from the target location on the fluid before the next laser shot, less splashing occurs. Accordingly, a laser pulse frequency of less than about 2 Hz may be chosen in order to allow the bubbles to migrate between pulsing of the laser. A 1 Hz firing rate may be used.

Figure 6:
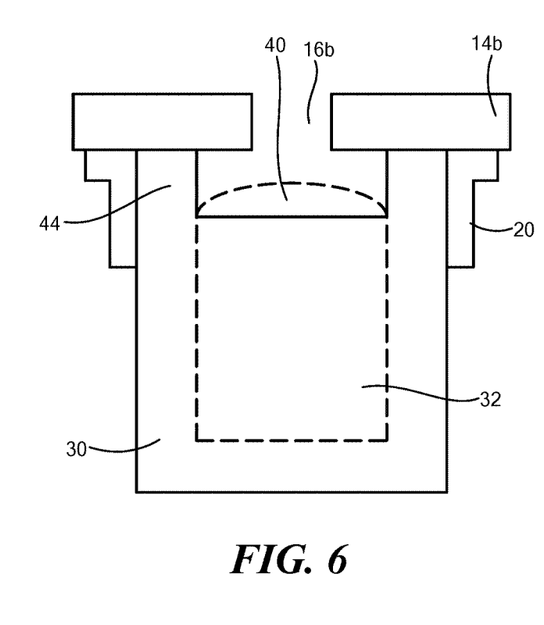
FIG. 6 is a cross sectional view showing how the sample holder of FIG. 1 is received in the positioner shown in FIG. 3.

Holder 30, FIGS. 4-5 preferably also include a stand-off of some kind such as rim 44 of a height sufficient to place the meniscus fluid at a predetermined and repeatable distance from the focusing lens of the handheld laser. As shown in FIG. 6, when the top of rim 44 seats against the outside of end plate 14b, the meniscus 40 is positioned about where a solid article would be located if the handheld analyzer was to be used as usual, to analyze a solid sample by engaging the end plate with the sample. Here, the distance between focusing lens 39 and the liquid sample meniscus is predetermined and repeatable.

Figure 7:
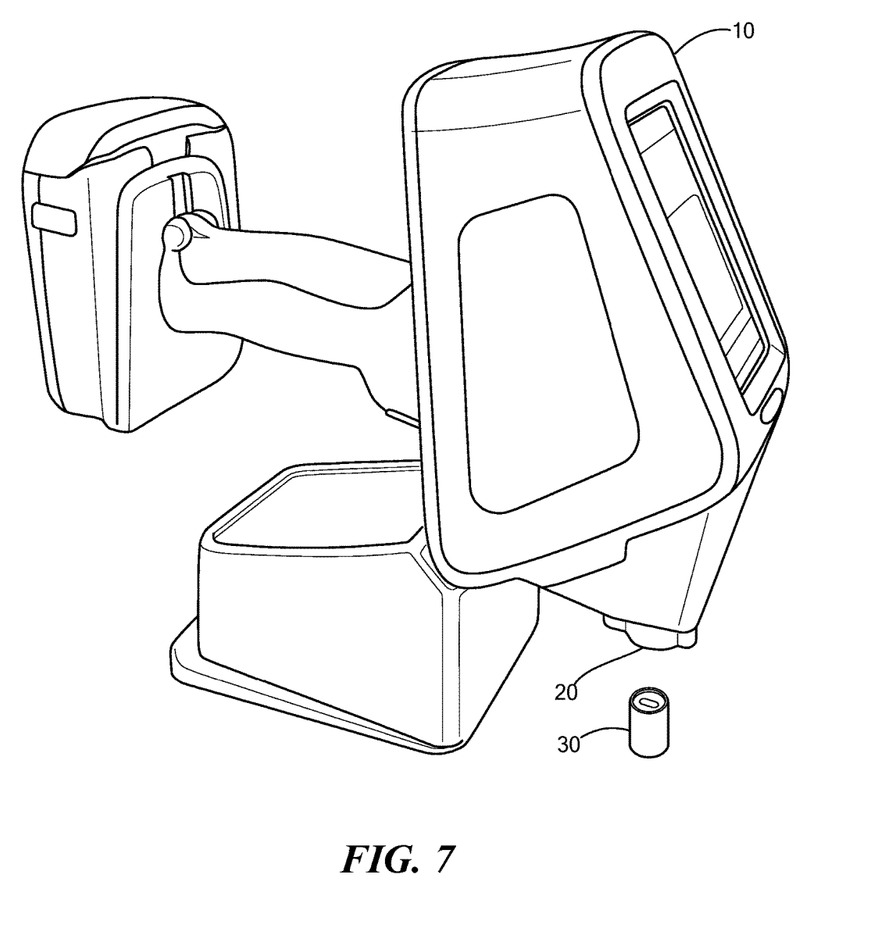
FIG. 7 is a three dimensional view showing how the analyzer can be used to analyze a liquid sample present in the sample holder.
Figure 8:
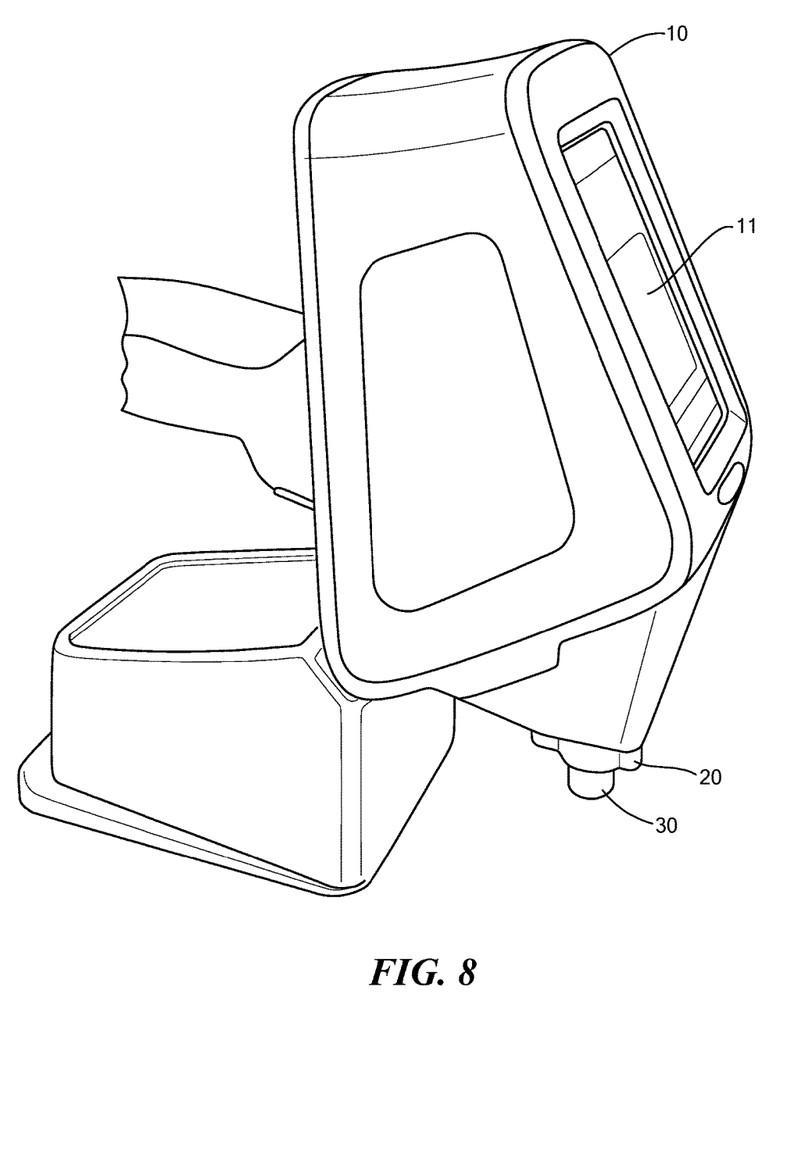
FIG. 8 is a schematic view similar to FIG. 7 but showing the sample holder now inserted into the positioner attached to the nose section of the analyzer.

In use, a liquid (e.g., lithium brine, oil, an alcoholic beverage, or the like) is loaded in the sample holder 30 as shown in FIGS. 5 and 7 using, for example, a pipette. As shown in FIG. 8, the sample holder 30 is loaded into positioner 20 and then the analyzer 10 is triggered to fire the laser and process the resulting spectrum to report, for example, on screen 11, the elements present in the liquid sample and their concentrations. In testing with lithium brine samples, the system reported lithium concentrations in known lithium reference samples with good accuracy. A purge gas such as argon may be used. U.S. Pat. No. 9,360,367 discloses a purge gas delivery system.

Figure 9:
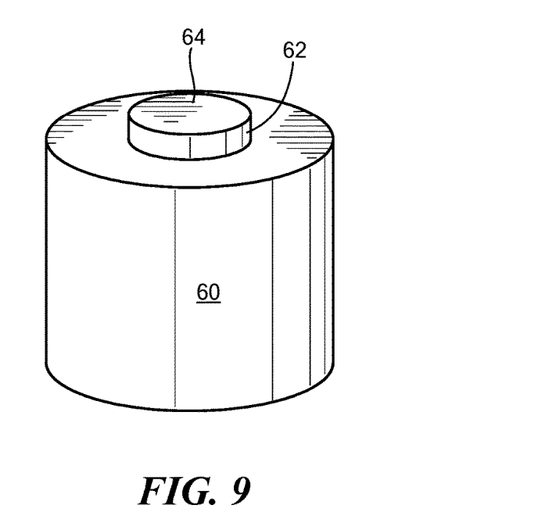
FIG. 9 is a schematic view showing an example of a calibration standard useful in connection with the invention.

FIG. 9 shows a calibration standard 60 (e.g., made of stainless steel) receivable in the socket 22, FIG. 3 of the positioner 20 for calibration of the analyzer. In the example shown, top post 62 has top surface 64 which is receivable through the opening 16, FIGS. 2-3 of the end plate 14b and into the nose section of the handheld analyzer spacing surface 64 a predetermined distance from the focusing lens of the analyzer.

Figure 10:
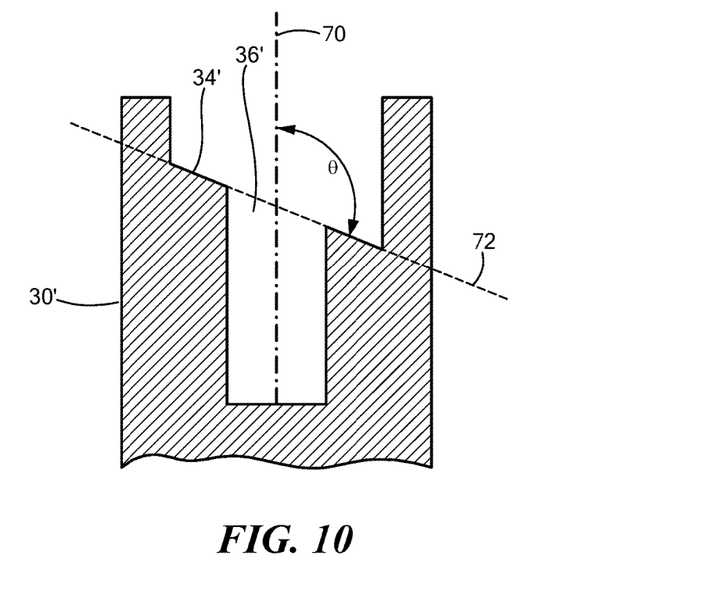
FIG. 10 is a schematic cross sectional view showing another embodiment of a sample holder with an angled interior surface.

In other examples, to move bubbles away from the site on the surface of the liquid to be analyzed which is struck by the laser beam, the handheld LIBS analyzer 10, FIG. 8 may be tilted during operation of the analyzer so any bubble will naturally move up the surface of the liquid meniscus by gravity. The same result can achieved as shown in FIG. 10 for sample holder 30' with surface 34' having opening 36' which lies on an axis 72 which is tilted at an angle θ relative to the longitudinal access 70 of the sample holder. Thus, θ may be greater than 90°.

The result, in one or more embodiments, is the system facilitating on-site liquid analysis using a LIBS analyzer. In preferred embodiments, the system is easy to use, cost effective, involves few or no moving parts, and provides accurate results. Besides analyzing the concentration of lithium and lithium brines, concentrations or impurities in oils or alcoholic beverages may a analyzed, and other liquids can be analyzed using the above described system and method.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A LIBS analysis system for liquids, the system comprising:
    a handheld LIBS analyzer with a nose section through which a laser beam passes;
    a sample holder positioner attached to the nose section of the hand held LIBS analyzer; and
    a sample holder receivable in the sample holder positioner and including:
        a container for liquid, and
        an opening for filling the container with liquid.

2. The system of claim 1 in which the nose section includes an end plate with an orifice therethrough for the laser beam and the positioner is affixed to the end plate.

3. The system of claim 2 in which the end plate is adapted for liquid samples and includes an enlarged orifice therethrough.

4. The system of claim 2 in which the positioner includes a socket about the end plate orifice and receiving the sample holder therein.

5. The system of claim 1 in which the sample holder opening is non-circular to dampen shock waves produced in the liquid by the laser beam.

6. The system of claim 5 in which the sample holder top opening is oval-shaped.

7. The system of claim 2 in which the sample holder further includes a standoff spacing the top opening from the end plate when the sample holder is placed in the positioner.

8. The system of claim 7 in which the standoff includes a rim about the opening.

9. The system of claim 1 in which the sample holder includes a top surface and the opening is in the top surface.

10. The system of claim 1 in which the sample holder is filled with liquid forming a liquid meniscus above the opening.

11. The system of claim 10 in which the handheld LIBS analyzer is configured to direct the laser beam at a location on the liquid meniscus other than at the apex of the liquid meniscus.

12. The system of claim 11 in which the handheld LIBS analyzer is configured to produce a pulsed laser beam at a frequency sufficient to allow any bubbles created in the liquid meniscus to migrate and/or dissipate.

13. The system of claim 12 in which said frequency is 2 Hz or less.

14. The system of claim 1 in which the handheld LIBS analyzer is configured to direct a laser beam at a location at the sample holder top opening other than its center.

15. The system of claim 1 in which said liquid is lithium brine.

16. The system of claim 1 in which said liquid is oil.

17. The system of claim 1 in which said liquid is an alcoholic beverage.

18. The system of claim 1 in which said handheld LIBS analyzer is configured with a purge gas delivery subsystem providing a purge gas at said nose section.

19. The system of claim 1 in which said sample holder has a longitudinal axis and the top opening is tilted along an axis at an angle to the longitudinal axis.

20. The system of claim 1 further including a calibration standard receivable in the positioner.

21. The system of claim 20 in which said calibration standard includes a top surface receivable into the nose section when the calibration standard is placed in the sample holder.

22. A method of analyzing liquids using a handheld LIBS analyzer, the method comprising:
    equipping the handheld LIBS analyzer with a sample holder positioner;
    loading a liquid into a sample holder configured to be inserted into the positioner;
    placing the sample holder into the positioner; and
    operating the handheld LIBS analyzer to analyze said liquid in the sample holder.

23. The method of claim 22 in which the positioner is affixed to an end plate of the analyzer.

24. The method of claim 23 in which the end plate is adapted for liquid samples and includes an enlarged orifice therethrough.

25. The method of claim 24 in which the sample holder is placed in a socket in the positioner disposed about the enlarged orifice.

26. The method of claim 22 in which the sample holder has a non-circular opening for the liquid to dampen shock waves produced in the liquid by the laser beam.

27. The method of claim 26 in which the sample holder opening is oval-shaped.

28. The method of claim 22 in which the sample holder is filled with liquid forming a liquid meniscus.

29. The method of claim 28 in which the handheld LIBS analyzer directs a laser beam at a location on the liquid meniscus other than at the apex of the liquid meniscus.

30. The method of claim 22 in which the handheld LIBS analyzer laser beam is pulsed at a frequency sufficient to allow any bubbles created to migrate and/or dissipate.

31. The method of claim 30 in which said frequency is 2 Hz or less.

32. The method of claim 22 in which said handheld LIBS analyzer provides a purge gas.

33. The method of claim 22 further including placing a calibration standard in the positioner.

34. The method of claim 22 further including tilting the handheld LIBS analyzer to encourage any bubbles formed to migrate.

35. A LIBS analysis system for liquids, the system comprising:
 a sample holder positioner attachable to the nose section of a hand held LIBS analyzer and including a socket;
 a sample holder receivable in the sample holder positioner socket and including:
 a container for a liquid sample, and
 an opening for filling the container with the liquid sample.

36. The system of claim 35 further including an end plate adapted for liquid samples and including an enlarged orifice therethrough, the end plate attachable to the analyzer and the positioner attachable to the end plate.

37. The system of claim 35 in which the sample holder opening is non-circular to dampen shock waves produced in the liquid.

38. The system of claim 32 in which the sample holder opening is oval-shaped.

39. The system of claim 35 in which the sample holder includes a top surface and the opening is in the top surface.

40. The system of claim 35 in which the sample holder container is filled with liquid forming a liquid meniscus above the opening.

41. They system of claim 35 in which said sample holder has a longitudinal access and the top opening it tilted along an axis at an angle to the longitudinal axis.

42. The system of claim 35 in which said system further includes a calibration standard receivable in the positioner socket.

* * * * *